US00PP20957P3

(12) United States Plant Patent
Fulcher

(10) Patent No.: US PP20,957 P3
(45) Date of Patent: Apr. 27, 2010

(54) *AGAPANTHUS* PLANT NAMED 'NORTHERN STAR'

(50) Latin Name: *Agapanthus hybrida*
Varietal Denomination: Northern Star

(76) Inventor: Richard John Fulcher, 1 Fourways Eggesford, Chumleigh, Devon (GB) EX18 7QZ ( * ) Notice: Subject to any disclaimer, the term of this patent is extended or adjusted under 35 U.S.C. 154(b) by 0 days.

(21) Appl. No.: 12/380,730

(22) Filed: Mar. 3, 2009

(65) Prior Publication Data

US 2009/0178170 P1 Jul. 9, 2009

(51) Int. Cl.
*A01H 5/00* (2006.01)

(52) U.S. Cl. ..... Plt./398

(58) Field of Classification Search ..... Plt./398
See application file for complete search history.

*Primary Examiner*—Annette H Para
(74) *Attorney, Agent, or Firm*—Mark P. Bourgeois

(57) ABSTRACT

A new cultivar of *Agapanthus* plant named 'Northern Star' that is characterized by green leaves with a violet base and a large number of violet flowers.

1 Drawing Sheet

Botanical classification: *Agapanthus hybrida.*
Variety denomination: 'Northern Star'.

BACKGROUND OF THE INVENTION

The present invention relates to a new and distinct cultivar of *Agapanthus* plant botanically known as *Agapanthus hybrida* and hereinafter referred to by the cultivar name 'Northern Star'.

'Northern Star' originated from a chance open pollination of a group of unnamed *Agapanthus* cultivars (not patented). 'Northern Star' was discovered and selected as a single plant within the progeny of the chance open pollination in an outdoor garden in Fourways, Eggesford, Devon, United Kingdom in the Summer of 1998.

Asexual reproduction of the new cultivar 'Northern Star' first occurred by tissue culture in 2002 in Fourways, Eggesford, Devon, United Kingdom. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Agapanthus* cultivar 'Northern Star'. These traits in combination distinguish 'Northern Star' as a new and distinct cultivar apart from other existing known varieties of *Agapanthus*.

1. *Agapanthus* 'Northern Star' exhibits green leaves with a violet base.
2. *Agapanthus* 'Northern Star' exhibits large violet flowers.
3. *Agapanthus* 'Northern Star' exhibits a large number of flowers.

The closest comparison cultivar is *Agapanthus* 'Nikki' (not patented). 'Northern Star' is distinguishable from 'Nikki' by the following characteristics:

1. 'Northern Star' exhibits larger and more numerous flowers than 'Nikki'.
2. 'Northern Star' exhibits a larger overall size than 'Nikki'.
3. 'Northern Star' exhibits longer scapes than 'Nikki'.

4. 'Northern Star' exhibits flowers that are darker violet-blue than the flowers of 'Nikki'.

BRIEF DESCRIPTION OF THE DRAWING

The accompanying photograph illustrates the distinguishing traits of *Agapanthus* 'Northern Star'. The plant in the photograph shows an overall view of a 1 year old plant grown outdoors in Fourways, Eggesford, Devon, United Kingdom. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Agapanthus* cultivar named 'Northern Star'. Data was collected in Fourways, Eggesford, Devon, United Kingdom from 1 year old outdoor grown plants. The time of year was August and the temperature range was 19–21 degrees Centigrade during the day and 10–12 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Northern Star' has not been tested under all possible conditions and phenotypic differences may be observed with variations in environmental, climatic, and cultural conditions, however, without any variance in genotype.

Botanical classification: *Agapanthus hybrida* 'Northern Star'.
Use: Ornamental Perennial.
Parentage: The exact parents of 'Northern Star' are unknown.
Vigor: High.
Growth habit: Upright.
Plant shape: Basal leaves with central flowering scapes.
Overall height: 100 cm. in height.
Overall width: 80 cm. in width.
Low temperature tolerance: −5° Centigrade.
High temperature tolerance: 40° Centigrade.

Propagation: Tissue culture.
Crop time: 6 months to produce a finished liner plant.
Root system: Thick, fleshy, white-grey in color.
Foliage:
*Leaf arrangement.*—Basal.
*Compound or single.*—Single.
*Quantity of leaves per plant.*—About 20.
*Texture.*—Leathery.
*Leaf shape.*—Linear.
*Leaf apex.*—Acute.
*Leaf base.*—Cuneate.
*Leaf length.*—57.5 cm. in length.
*Leaf width.*—22.5 cm. in width.
*Pubescence.*—Absent.
*Leaf margin.*—Entire.
*Young leaf color* (*lower surface*).—137A.
*Young leaf color* (*upper surface*).—137A.
*Mature leaf color* (*lower surface*).—137A.
*Mature leaf color* (*upper surface*).—137A, base 92A.
*Vein color* (*under surface*).—137A.
*Vein color* (*upper surface*).—137A.
*Venation pattern.*—Parallel.
*Leaf attachment.*—Sessile.
Flower:
*Inflorescence arrangement.*—Campanulate flowers arranged in umbels on erect scapes.
*Quantity of flowers and buds per plant.*—3,500.
*Natural flowering season.*—August.
*Fragrance.*—None.
*Inflorescence size.*—18 cm. in length and 16 cm. in width.
*Quantity of flowers per inflorescence.*—Approximately 150.
*Flower bud length.*—25 mm. in length.
*Flower bud diameter.*—8 mm. in diameter.
*Flower bud shape.*—Oblong.
*Bud color.*—93A.
*Flower aspect.*—Upright.
*Flower shape.*—Campanulate.
*Flower dimensions.*—30 mm. in diameter and 33 mm. in height.
*Flower longevity.*—Approximately 5 weeks.
*Flower longevity as a cut flower.*—10 days.
*Tepal texture.*—Smooth.
*Number of tepals.*—8.
*Fused or unfused.*—Lower 50% are fused.
*Tepal shape.*—Oblanceolate to ovate.
*Tepal margin.*—Repand.
*Tepal apex.*—Rounded.
*Tepal base.*—Rounded.
*Tepal length.*—33 mm. in length.
*Tepal width.*—11 mm in width.
*Tepal color when opening* (*upper side*).—93A.
*Tepal color when opening* (*under side*).—89D.
*Tepal color fully opened* (*upper side*).—93A.
*Tepal color fully opened* (*under side*).—89D.
*Self-cleaning or persistent.*—Persistent.
*Peduncle.*—Peduncle dimensions: 90 cm. in length and 10 mm. in diameter. Peduncle angle: 0° from vertical. Peduncle color: 137A. Peduncle strength: Strong.
*Pedicels.*—Pedicel dimensions: 45 mm. in length and 1.5 mm. in diameter. Pedicel color: 137A. Pedicel strength: Moderate.
Reproduction organs:
*Stamen number.*—Average 6.
*Anther shape.*—Oval.
*Anther size.*—Average 2 mm.
*Anther color.*—97B.
*Amount of pollen.*—High.
*Pollen color.*—4A.
*Pistil number.*—Average 1.
*Pistil length.*—Average 32 mm. in length.
*Stigma shape.*—Trifid.
*Stigma color.*—106B.
*Style length.*—30 mm.
*Style color.*—107A.
*Ovary color.*—133A.
Fruit/seed:
*Fruit type.*—Capsule.
*Quantity of fruit.*—1 capsule per flower, 100 capsules per umbel.
*Fruit dimensions.*—20 mm. in length and 11 mm. in diameter.
*Fruit color.*—136A.
*Seed size.*—3 mm. in length and 1 mm. in diameter.
*Seed color.*—202A.
Disease and pest resistance: Plants of the new cultivar have not been observed for disease and pest resistance.

The invention claimed is:
1. A new and distinct variety of *Agapanthus* plant named 'Northern Star' as described and illustrated.

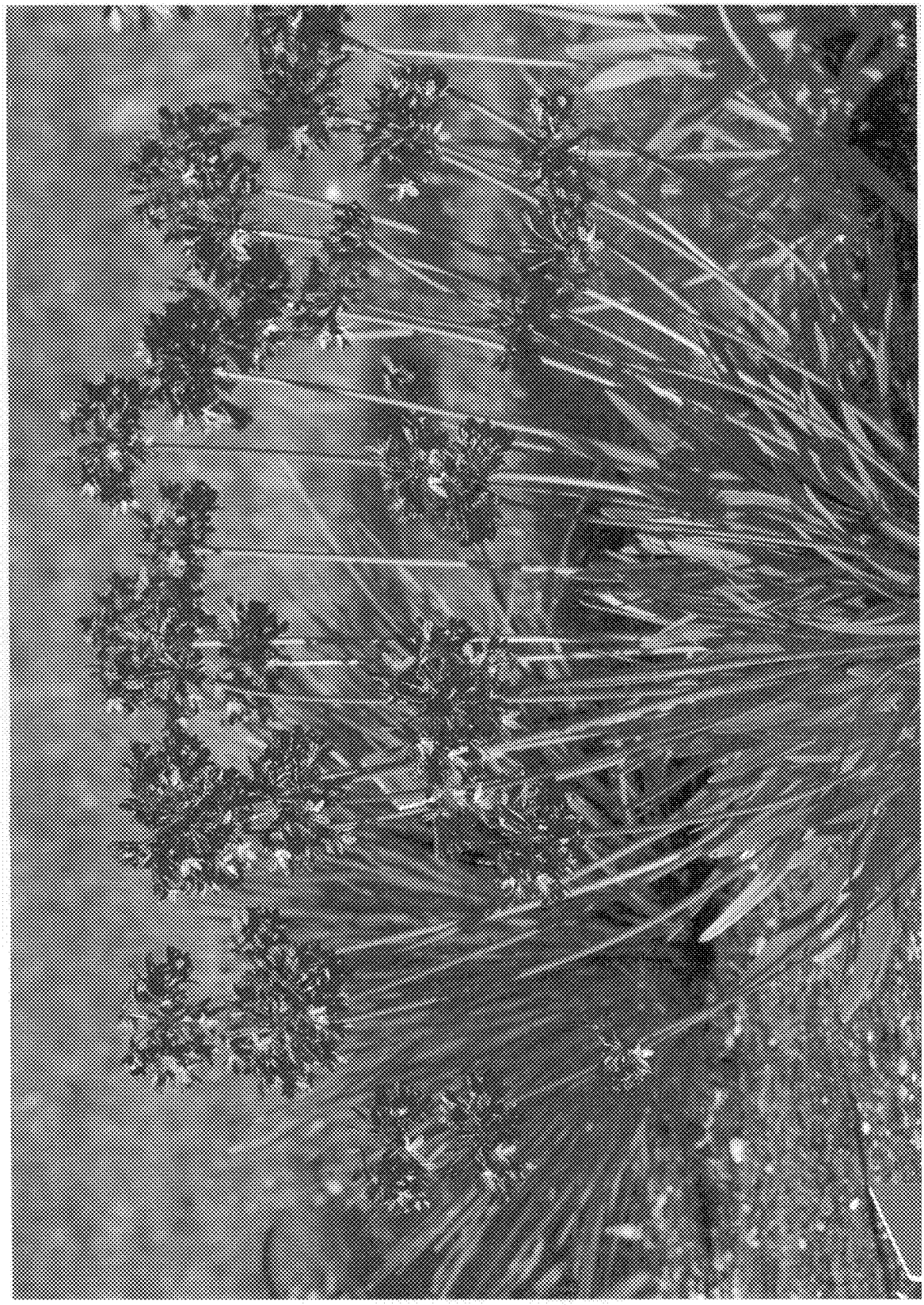

* * * * *